United States Patent [19]

Koike et al.

[11] Patent Number: 4,845,747
[45] Date of Patent: Jul. 4, 1989

[54] APPARATUS FOR MEASURING DENSITY OF VERTEBRAE OR THE LIKE

[75] Inventors: Kiyoshi Koike, Shizuoka; Takuo Fujita, Hyogo; Rikushi Morita, Kyoto, all of Japan

[73] Assignee: Hamamatsu Photonics Kabushiki Kaisha, Shizuoka, Japan

[21] Appl. No.: 928,405

[22] Filed: Nov. 10, 1986

[30] Foreign Application Priority Data

Nov. 8, 1985 [JP] Japan .......................... 60-171896[U]

[51] Int. Cl.⁴ ............................................... H05G 1/02
[52] U.S. Cl. ..................................... 378/208; 378/209
[58] Field of Search ................ 378/208, 209; 297/349

[56] References Cited

U.S. PATENT DOCUMENTS

| | | | |
|---|---|---|---|
| 1,442,027 | 1/1923 | Levenson | 378/208 |
| 3,585,386 | 6/1971 | Horton | 378/208 |
| 4,229,656 | 10/1980 | Iversen et al. | 378/206 |

*Primary Examiner*—Carolyn E. Fields
*Assistant Examiner*—David P. Poita
*Attorney, Agent, or Firm*—Finnegan, Henderson, Farabow, Garrett & Dunner

[57] ABSTRACT

Apparatus for measuring the density of vertebrae or the like, comprises gamma ray emission means for emitting gamma rays within a predetermined target area; detecting means for detecting the gamma rays passing through the target area; and rotatable positioning means between the emission means and the detecting means for supporting a subject and exposing the subject to the gamma rays in the target area at a plurality of different angles.

6 Claims, 1 Drawing Sheet

APPARATUS FOR MEASURING DENSITY OF VERTEBRAE OR THE LIKE

BACKGROUND OF THE INVENTION

The present invention relates to an apparatus for measuring the density of vertebrae or the like, in which a portion to be inspected (for example, vertebrae) of a subject or the like can take a plurality of predetermined positions between a gamma ray source and a detecting area.

The inventors of the present invention have developed an apparatus for measuring the density of an object having a small transmission factor. In this apparatus, a gamma ray source is used for emitting gamma rays within a predetermined solid angle from a fixed point. The gamma rays transmitted through a subject to be measured are collimated by a collimator. The collimator is situated a predetermined spatial distance along an axial line from the gamma ray source corresponding to the solid angle, and includes a number of capillaries directed to the fixed point. A scintillator is disposed close to the collimator, and photomultipliers are arranged close to each other with their photocathodes facing the scintillator. A position-operating integrated circuit estimates incident positions on the basis of an incident unit when light of the scintillator impinging onto the photomultipliers is temporally separated. The circuit integrates an incident frequency at every incident position, thereby obtaining data relating to density of an object having a small transmission factor by irradiating the object with gamma rays for a predetermined time.

The following problems arise when data as to density of vertebrae of a subject is to be obtained. Vertebrae are considered to be the most important bodily portion in measurement of bone density. Around the lumbar vertebrae, there are arteries in which sedimation of calcium may occur, and calcium absorbs gamma rays. In the case where measurement is performed from the front of a subject, there is no problem of simultaneous transmission through bisymmetrical bones. However, there is a serious problem in that arteries may be superimposed upon bones. If measurement is performed from the side of the subject, arteries are less likely to be superimposed upon bones, so that the measurement can be carried out with no problem even in the case of a subject in which calcium has settled in the arteries. Therefore, it is desirable to be able to measure the subject from a plurality of directions.

In order to keep a subject at a predetermined position during photographing or the like by exposure to gamma rays, a holder (for example a chair) has been used to fix the position of the subject. Although this enables a subject to be kept at a predetermined position, the conventional apparatus is not suitable for performing measurement from different angles.

SUMMARY OF THE INVENTION

An object of the present invention is to provide an apparatus for measuring the density of vertebrae or the like, in which the vertebrae of a subject can be measured quickly from a plurality of directions.

Additional objects and advantages will be obvious from the description which follows, or may be learned by practice of the invention.

In order to achieve the above-mentioned object, the apparatus for measuring density of vertebrae or the like according to the present invention comprises gamma ray emission means for emitting gamma rays within a predetermined target area; detecting means for detecting the gamma rays passing through the target area; and rotatable positioning means between the emission means and the detecting means for supporting a subject and exposing the subject to the gamma rays in the target area at a plurality of different angles.

Preferably, the positioning means includes a seat having a frame thereon for supporting a human subject in a predetermined position on the seat. It is also preferred that the positioning means include rotating means for moving the seat between preset positions.

The rotating means may include a motor and gear means connected to the motor for automatically rotating the seat. The rotating means also preferably includes a first preset position wherein the subject is oriented to face the gamma ray target area, and a second preset position wherein the subject is oriented at 90° to the first preset position. The seat also may include foot support means for supporting the feet of a subject.

BRIEF DESCRIPTION OF THE DRAWINGS

The accompanying drawings, which are incorporated in and constitute a part of the specification, illustrate an embodiment of the invention, and, together with the description, serve to explain the principles of the invention. Of the drawings:

FIG. 2 is a schematic view showing the arrangement in plan of the above-mentioned apparatus for measuring density of vertebrae or the like.

DETAILED DESCRIPTION OF THE PREFERRED EMBODIMENT

Figure 1:
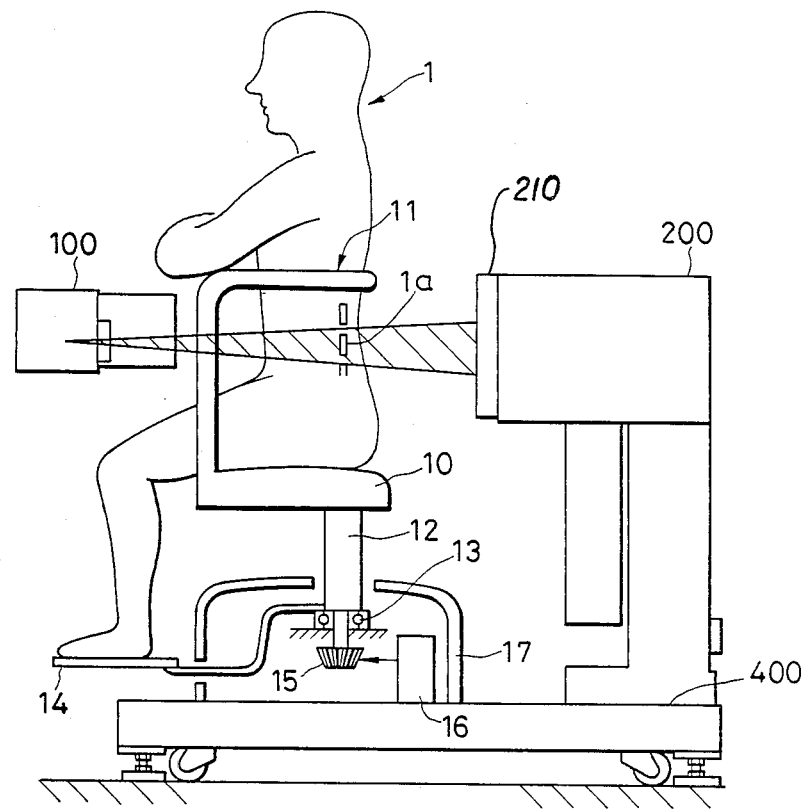
FIG. 1 is a side view showing an embodiment of the apparatus for measuring density of vertebrae or the like according to the presnt invention.
Figure 2:
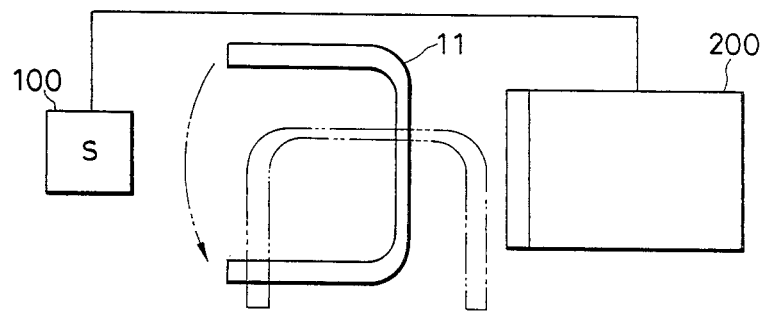

In accordance with the invention, the apparatus for measuring the density of vertebrae or the like, comprises gamma ray emission means for emitting gamma rays within a predetermined target area; detecting means for detecting the gamma rays passing through the target area; and rotatable positioning means between the emission means and the detecting means for supporting a subject and exposing the subject to the gamma rays in the target area at a plurality of different angles. As embodied herein the positioning means includes a seat having a frame thereon for supporting a human subject in a predetermined position on the seat, and rotating means for moving the seat between preset positions. A first preset position may be used wherein the subject is oriented to face the gamma ray target area, and a second preset position is preferred wherein the subject is oriented at 90° to the first preset position. Reference will now be made in detail to the present preferred embodiment of the invention, an example of which is illustrated in the accompanying drawings. The whole apparatus is mounted on a castor 400, and a detecting portion 200 is supported on the castor so as to face a ray source portion 100. A portion (vertebrae) of a subject to be measured is arranged on an axial line between the ray source portion 100 and the detecting portion 200. The ray source using a radioactive material 153 Gd is arranged so as to emit gamma rays within an area defining a solid angle in a plane from the ray source to the detector. This angle forms a cross-section on a plane passing through a circular cone in front of the ray source. Preferably, the angle is about 16 degrees.

The detecting portion 200 is provided with a collimator 210, a scintillator, and photomultipliers for detecting scintillation light from the scintillator. Scattered gamma rays or the like are eliminated by the collimator, and the scintillator is made to emit light by the gamma rays within the above-mentioned solid angle. The luminous emission from the scintillator is photoelectrically multiplied by one photomultiplier or more. An operation circuit detects an incident position on X-Y coordinates with the center of the scintillator as an origin thereof, and generates a suitable display, as well as storing the data.

As shown in FIG. 1, a subject 1 is positioned in a seat in the form of a pivot chair 10 on the castor 400. The seat 10 is mounted on a rotary shaft 12 rotatably supported by rotary bearings 13. A foot reception 14 is provided integrally with the rotary shaft 12. A frame 11 also is provided in connection with the seat 10. The frame 11 is arranged so as not to block the gamma rays from the ray source at least in the position as shown in FIG. 1 and a second position with the subject turned by 90° degrees from the first-mentioned position. When a typical subject 1 sits on the seat 10 and places his arms on the frame 11, vertebrae 1a of the subject 1 are brought onto the center axis line of the gamma ray source (a center line of a cone) owing to the frame 11.

A gear 15 constituting a part of a rotary mechanism is provided at a lower end of the rotary shaft 12. The gear 15 is rotated by the output of a driving device 16 having an electric motor. The seat 10 is rotated a desired angle when the subject is mounted on the seat. The amount of rotation can be automatically set to a predetermined angle, e.g., a position directly opposite the ray source and another position rotated therefrom by 90 degrees. An encoder also can be provided in relation to the shaft so as to detect the rotational position.

Though an electric motor is used for rotating the seat in the embodiment described above, it is possible to rotate the seat manually. In this case, click mechanisms are provided at suitable positions to lock the seat.

According to the apparatus described above, it is possible to obtain data about vertebrae of a subject if the subject is made to sit on the seat and respective data are collected at the above-mentioned two positions of the seat.

Thus, data with respect to a portion to be measured can be obtained quickly at different positions. In the apparatus described above, necessary data from one direction can be obtained by irradiation for two-three minutes. Accordingly, six minutes are enough to obtain respective data at two positions, one being a position directly opposite to the ray source and a position rotated therefrom by 90 degrees. If the data are obtained respectively at the above-mentioned two positions, the thickness of bones can be determined, and calculation of the density of the bones can be carried out extremely easily.

The embodiment described in detail above can be modified in various ways within the scope of the present invention. A case of measuring density of vertebrae of a subject is shown merely by way of example in the embodiment described above, however, the apparatus obviously is applicable for measuring any portions of a subject other than vertebrae.

What is claimed is:

1. Apparatus for measuring the density of vertebrae, comprising:
    gamma ray emission means for emitting gamma rays within a predetermined target area;
    detecting means for detecting the gamma rays passing through the target area; and
    rotatable positioning means between the emission means and the detecting means for supporting a subject and exposing the subject in at least two predetermined angular positions relative to the gamma rays in the target area, said rotatable positioning means including means to automatically rotate said positioning means between said at least two predetermined angular positions.

2. The apparatus of claim 1 wherein the positioning means includes a seat having a frame thereon for supporting a human subject in a predetermined position on the seat.

3. The apparatus as recited in claim 1, wherein the gamma rays are emitted from a fixed point and the detecting means includes a collimator for eliminating gamma rays outside the predetermined target area, said collimator including capillaries directed toward said fixed point.

4. The apparatus of claim 2 wherein the means to rotate includes a motor and gear means connected to the motor for automatically rotating the seat.

5. The apparatus of claim 1 wherein the subject is oriented to face the gamma ray target area in the first predetermined angular position, and wherein the subject is oriented at 90° to the first predetermined angular position when in the second predetermined angular position.

6. The apparatus of claim 2 wherein the seat includes foot support means for supporting the feet of a subject.

* * * * *